United States Patent [19]

Rogers et al.

[11] Patent Number: 4,550,192

[45] Date of Patent: Oct. 29, 1985

[54] FLUOROPHENOXYPHENOXYPROPION-ATES AND DERIVATIVES THEREOF

[75] Inventors: Richard B. Rogers; B. Clifford Gerwick, III, both of Concord, Calif.

[73] Assignee: The Dow Chemical Company, Midland, Mich.

[21] Appl. No.: 528,711

[22] Filed: Sep. 1, 1983

[51] Int. Cl.⁴ .............................................. C07C 69/76
[52] U.S. Cl. ...................................... 560/62; 560/63; 71/108; 71/109; 562/471; 564/170; 564/171
[58] Field of Search ...................... 560/62, 63; 71/108, 71/109; 564/170; 562/471

[56] References Cited

U.S. PATENT DOCUMENTS 3,954,442  5/1976  Beeker et al. ........................ 560/11

FOREIGN PATENT DOCUMENTS 2639796  3/1977  Fed. Rep. of Germany ........ 560/11

Primary Examiner—Paul J. Killos

[57] ABSTRACT

Novel fluorophenoxyphenoxypropionates and derivatives thereof possess herbicidal activity selectively in the presence of broadleaf crops. Preemergent and postemergent applications are contemplated.

55 Claims, No Drawings

FLUOROPHENOXYPHENOXYPROPIONATES AND DERIVATIVES THEREOF

BACKGROUND OF THE INVENTION

The present invention relates to novel fluorophenoxyphenoxypropionates and derivatives thereof which are useful as herbicides. The present invention also relates to herbicidal compositions containing these novel compounds; to methods of using these compounds for the control of weeds in non-crop areas as well as in the presence of valuable crops; and to novel intermediates used to make these compounds.

Various 4-phenoxy-phenoxy-propionic acids are known as herbicidal agents. U.S. Pat. No. 4,332,961 discloses α[4-(4-trifluoromethylphenoxy)phenoxy]alkane carboxylic acid and derivatives thereof wherein the "4-trifluoromethylphenoxy group" may optionally contain a chloro substituent. U.S. Pat. No. 4,332,960 discloses α[4-(2'-hydrogen or halogen-4'-trifluoromethyl-phenoxy)phenoxy]propionic acid and derivatives thereof wherein hydrogen is the preferred substituent at the 2' position. Both of these patents teach the compounds disclosed in them as possessing herbicidal activity.

U.S. Pat. No. 4,370,489 discloses α[4-(2'-chloro-4'-bromo-phenoxy)-phenoxy]propionic acid and derivatives thereof as possessing herbicidal activity.

Heretofore, α[4-(2'-fluoro-4'-substituted-phenoxy)-phenoxy]propionic acids and agriculturally acceptable derivatives thereof have not been disclosed.

SUMMARY OF INVENTION

The present invention is directed to fluorophenoxyphenoxypropionates of the formula (I):

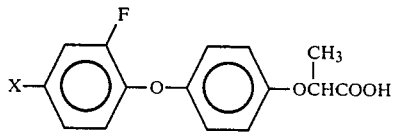

(I)

wherein
X represents —Cl, —CF$_3$, —I, —Br, —OCF$_3$, —CF$_2$Cl, —CF$_2$H or —OCF$_2$CCl$_2$H, and
agriculturally acceptable derivatives (salts, amides and esters) thereof.

The compounds of the above Formula I, hereinafter referred to as "active ingredients", have been found to be active as herbicides in the presence of broadleaf crops and are unexpectedly superior in activity compared to compounds known in the art. Compounds of Formula (I), above, wherein X is —Cl or —Br, are surprisingly selective to small grain crops, such as wheat and barley, i.e., substantially non-phytotoxic to small grain crops. Accordingly, the present invention also encompasses herbicidal compositions containing one or more active ingredients as well as methods of controlling unwanted vegetation. Such methods comprise, for example, applying a herbicidally effective amount of one or more active ingredients preemergently or postemergently to the locus of the undesired vegetation, and particularly to the locus where a valuable crop is to germinate and grow.

DETAILED DESCRIPTION OF THE INVENTION

The term "herbicide" is used herein to mean an active ingredient which controls or adversely modifies the growth of plants. By "growth controlling" or "herbicidally-effective" amount is meant an amount of active ingredient which causes an adversely modifying effect and includes deviations from natural development, killing, regulation, dessication, retardation, and the like.

The term "plants", when used herein, is meant to include germinant seeds, emerging seedlings, rhizomes, stolons and other underground propagules, as well as established vegetation.

The term "halogen" when used herein is meant to include F, Cl, I and Br.

The term "agriculturally acceptable salts, amides and esters", when used to describe the active ingredients disclosed herein, is meant to encompass any salt, amide, ester or derivative of said active ingredients (acids) which
(1) does not substantially affect the herbicidal activity of said active ingredients, or
(2) is or can be hydrolyzed and/or oxidized in plants or soil to a carboxyl moiety that is in undissociated and-/or dissociated form. Agriculturally acceptable derivatives of the active ingredients include compounds of the formula:

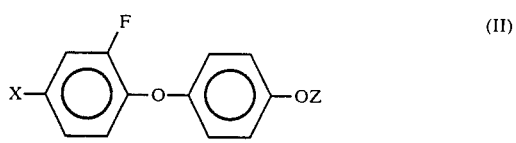

(II)

wherein
X represents —Cl, —CF$_3$, —I, —Br, —OCF$_3$, —CF$_2$Cl, —CF$_2$H or —OCF$_2$CCl$_2$H; and
Z represents an organic moiety containing N, O or S atoms, a metallic cation, an ammonium cation, or an organic amine cation and is or can be hydrolized and/or oxidized in plants or soil to a carboxyl moiety that is in undissociated and/or dissociated form.

Z moieties include, but are not limited to

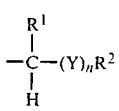

wherein
Y represents a saturated or unsaturated alkyl group containing an even number of carbon atoms, preferably from 2 to 18 carbon atoms;
n represents 0 or 1;
R$^1$ represents H or a C$_1$-C$_3$ alkyl group; and
R$^2$ represents moieties corresponding to one of the following formulae:

(1)

(2)

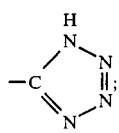 (3)

 (4)

wherein Hal is halogen;

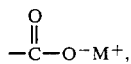 (5)

wherein M represents a metallic cation, ammonium cation or an organic amine cation, typically, but not exclusively, containing alkyl (saturated or unsaturated), alicyclic, heterocyclic or aromatic groups, all unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl;

$-CH_2OR^3$; (6)

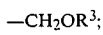 (7)

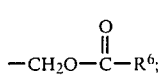 (8)

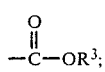 (9)

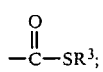 (10)

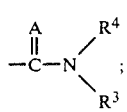 (11)

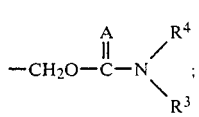 (12)

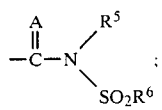 (13)

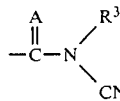 (14)

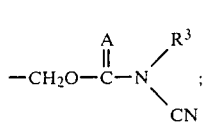 (15)

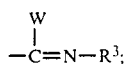 (16)

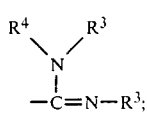 (17)

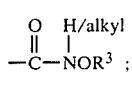 (18)

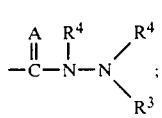 (19)

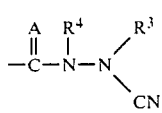 (20)

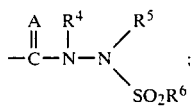 (21)

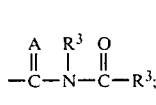 (22)

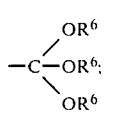 (23)

$-C(SR^6)_3$; (24)

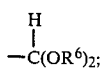
(25)

(26)

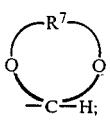
(27)

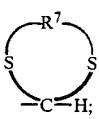
(28)

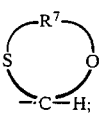
(29)

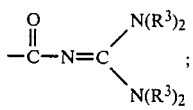
(30)

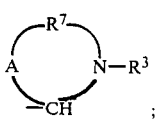
(31)

wherein
W represents —OR$^6$, —SR$^6$ or halogen;
A represents O or S;
R$^3$ represents H or R$^6$;
R$^4$ represents H, alkoxy or R$^6$;
R$^5$ represents H, a metallic cation or R$^6$; and
R$^6$ represents an alkyl (saturated or unsaturated), alicyclic, heterocyclic or aromatic group, unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl;

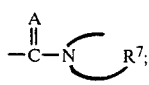
(32)

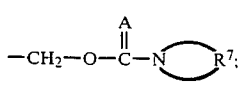
(33)

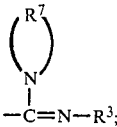
(34)

(35)

where B is O, S or N; or

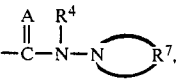
(36)

where R$^7$ completes an unsubstituted or substituted heterocyclic ring system and A represents O or S.

R$^2$ is preferably a carboxylic acid group, an alkali or alkaline earth metal salt thereof, an ammonium or organic amine salt thereof or a lower alkyl ester thereof, wherein "lower alkyl" includes straight, branched or cyclic saturated or unsaturated alkyl groups containing no more than 6 carbon atoms. Preferably, n is 0 and R$^1$ is methyl.

In Formula (II) above, the aliphatic groups preferably contain 1 to 6 carbon atoms, the alkenyl and alkynyl groups preferably contain 2 to 6 carbon atoms, the alicyclic groups preferably contain 3 to 6 carbon atoms and the aromatic moiety is preferably phenyl, although other ring systems, including heterocyclic ring systems, may be employed if desired.

In Formula (II) above, X is preferably CF$_3$, Br or Cl. Most preferred are the compounds in which X is CF$_3$, Br or Cl, and z is

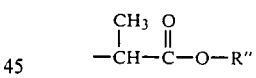

wherein R'' is hydrogen, methyl, ethyl, propyl, isopropyl, methoxypropyl, isobutyl or n-butyl.

The phenoxyphenoxy compounds of Formula (II), also referred to "active ingredients", above are prepared employing procedures analogous to well known procedures for preparing known phenoxyphenoxyalkanecarboxylic acids and derivatives thereof. U.S. Pat. Nos. 4,332,960; 3,954,442; 4,332,961; 4,384,135 and 4,370,489 describe such procedures and are all incorporated herein by reference. For example, some of the compounds of Formula (II) above are prepared by reacting an appropriately substituted 1,2-difluorobenzene with an alkali or alkaline earth metal salt of an appropriate hydroxyphenoxy compound in a suitable solvent medium, such as dimethylsulfoxide (DMSO), dimethylformamide (DMF), N-methylpyrollidone, hexamethylpyrophosphoramide or tetrahydrofuran (THF). The reaction is advantageously carried out at an elevated temperature of from about 65° C. to about 220° C. This reaction can be characterized as follows:

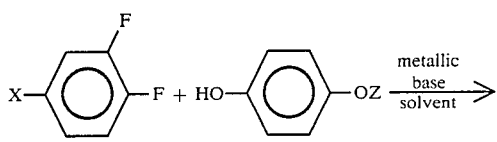

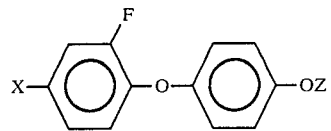

wherein X and Z are as hereinbefore defined. This reaction is preferred when preparing compounds of Formula II wherein X is $CF_3$.

Compounds of Formula (II) above wherein X is —CL or —Br are preferably prepared by reacting an alkali or alkaline earth metal salt of 4-(4'-chloro or bromo-2'-fluorophenoxy)phenol with an halo-Z compound, wherein Z is as defined in Formula (II), in a suitable solvent medium, such as, DMSO, DMF, THF, N-methylpyrrolidone or hexamethylpyrophosphoramide. This reaction is advantageously carried out at an elevated temperature of from about 80° C. to about 220° C. This reaction can be characterized as follows:

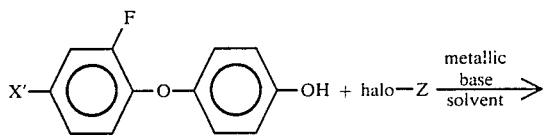

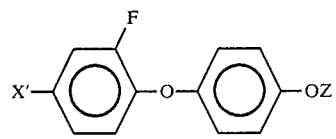

wherein X' is Cl or Br, Z is as hereinbefore defined and the metallic base is a base, such as, for example $Na_2CO_3$ or $K_2CO_3$.

4-(4'-(substituted)-2'-fluorophenoxy)phenol and salts thereof are novel intermediate compounds and are within the scope of the present invention. These intermediates can be prepared by hydrogenating 4-(4'-(substituted)-2'-fluorophenoxy)nitrobenzene with hydrogen in the presence of a Raney nickel catalyst. This reaction can be characterized as follows:

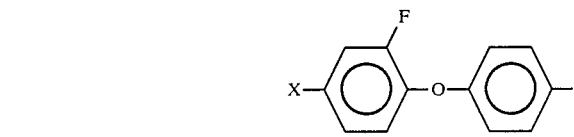

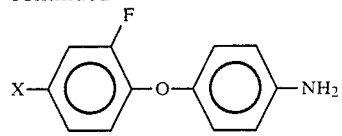

wherein X is as defined hereinbefore. 4-(2'-Fluoro-4'-(substituted)phenoxy)benzeneamine, also a novel compound and contemplated by the present invention, is reacted with fluoboric acid ($HBF_4$), sodium nitrite and water to form the tetrafluoroborate of 4-(-4'-(substituted)-2'-fluorophenoxy)benzene diazonium. This reaction can be characterized as follows:

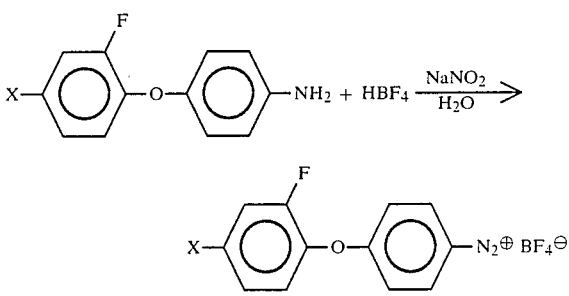

4-(2'-fluoro-4'-substituted phenoxy)benzenediazonium tetrafluoroborate, another novel compound and contemplated by the present invention, is reacted with (a) aqueous acid with heat or (b) an alkali metal trifluoroacetate in trifluoroacetic and water in accordance with the procedures taught in D. E. Horning et al., *Can. J. Chem.*, 51, 2347, (1973) which is incorporated herein by reference, resulting in the formation of 4-(2'-fluoro-4'-chlorophenoxy)phenol. These reactions can be characterized as follows:

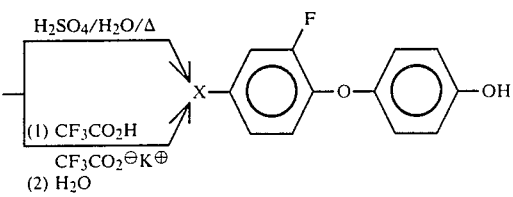

Preferred compounds of the present invention are the compounds of Formula (I) above wherein X represents —$CF_3$, —Br or —Cl, i.e. 4(2'-fluoro-4'-(chloro, bromo or trifluoromethyl)phenoxy)phenoxy propionic acid and agriculturally acceptable derivatives thereof. These preferred compounds are prepared by reacting the appropriate starting materials employing the procedures set forth above. The 4'-trifluoromethyl-2'-fluorophenoxyphenoxy propionates are prepared by reacting 1,2-difluoro-4-trifluoromethylbenzene with a salt of 4-hydroxyphenoxypropionic acid or a derivative thereof, i.e., an ester, or amide derivative of the 4-hydroxyphenoxypropionic acid. This reaction can be characterized as follows:

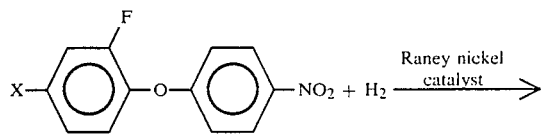

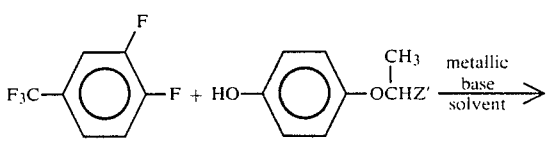

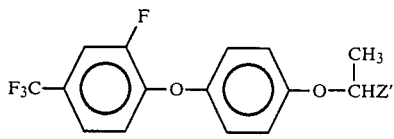

wherein

Z' represents —CO₂H (the acids), —CO₂M', —CO₂R⁸, —COSR⁸, —CONR₂⁹, —CSNH₂, —CN, —CH₂OR⁹ or —CH₂O₂CR⁹;

M' represents Li, Na, K, Mg, Ba or Ca, and corresponds to the cation of the metallic base, or N(R¹⁰)₄;

R⁸ represents C₁–C₈ alkyl or C₃–C₆ alkoxyalkyl;

each R⁹ independently represents H or C₁–C₄ alkyl; and

R¹⁰ independently represents H, C₁–C₄ alkyl or C₂–C₃ hydroxyalkyl.

The 4'-chloro-2'-fluorophenoxyphenoxy propionates are prepared by reacting a 4-(4'-chloro-2'-fluorophenoxy)phenol with a halopropionate in the presence of a base and solvent as described above. This reaction can be characterized as follows:

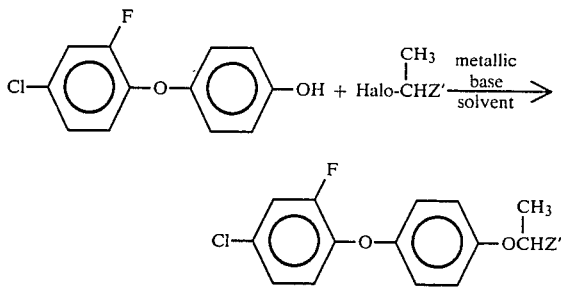

wherein Z' is as defined above.

The 4'-bromo-2'-fluorophenoxy propionates are prepared by reacting a 4-(4'-bromo-2'-fluorophenoxy)phenol with a halopropionate in the presence of a base and solvent as described above. This reaction can be characterized as follows:

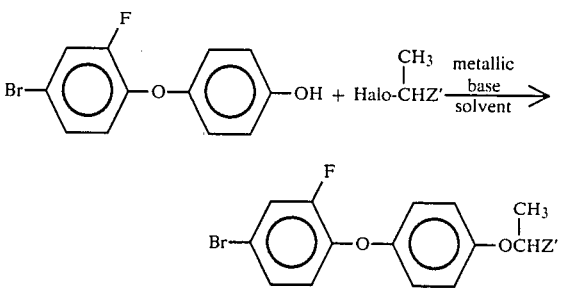

wherein Z' is as defined above.

The terms "C₁–C₄ alkyl" and "C₁–C₈ alkyl" refer to different size alkyl groups which may be straight, branched, or cyclic, when the group contains at least three carbon atoms, and, contain 1–4 or 1–8 carbon atoms respectively. The terms "C₂–C₃ hydroxyalkyl" and "C₃–C₆ hydroxyalkyl" refer to different size hydroxyalkyl groups having 2–3 or 3–6 carbon atoms, respectively, and the alkyl portion may be straight or branched, or cyclic when the group contains at least three carbon atoms.

Once prepared, the compounds of the present invention are recovered employing standard, well-known, extraction and purification techniques, such as, for example, solvent extraction with ether.

The following examples illustrate the practice of the present invention but should not be construed as limiting its scope. No attempt has been made to balance any equations described herein.

EXAMPLE 1

Preparation of α[4-(2'-fluoro-4'-trifluoromethylphenoxy)phenoxy]propionic acid methyl ester

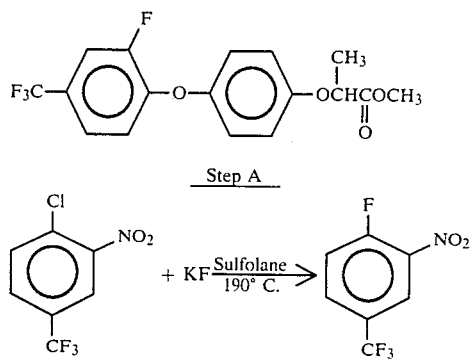

A stirred mixture of potassium fluoride (58 grams (g), 1 mole) and potassium carbonate (2 g) in sulfolane (300 ml) was subjected to vacuum distillation until 75 ml of liquid had distilled. This effectively removes any moisture from the system. The distillation head was removed and 4-chloro-3-nitrobenzotrifluoride (95 g, 0.42 mole) was added. The resulting mixture was heated at 190° C. for two hours, then allowed to cool to approximately 100° C. A 6 inch Vigreaux column was added to the reaction flask, and the product rapidly distilled under vacuum (~1 mm). The light yellow liquid so obtained was mostly the desired 4-fluoro-3-nitrobenzotrifluoride but contained small amounts of sulfolane (~4 percent) and starting material. This liquid was dissolved in pentane (600 ml), washed with water (3×500 ml), then dried (MgSO₄). Removal of the solvent and distillation of the yellow residual liquid gave 59 g (67 percent) of the desired product which had a boiling point (b.p.) of 51° C. at ~1 mm. The nuclear magnetic resonance (NMR) (CDCl₃) spectra was consistent with the assigned structure.

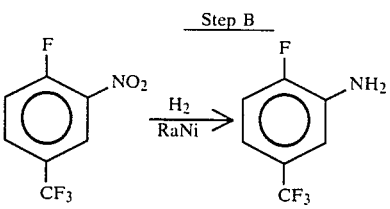

A mixture of 4-fluoro-3-nitrobenzotrifluoride (59 g, 0.282 mole) and Raney Nickel (RaNi) (Aldrich, 5-spoonula scoops) in ethanol (350 ml) was hydrogenated on a Paar apparatus (starting pressure=50 psi) until the theoretical amount of hydrogen had been consumed (~7 hours). The catalyst was filtered off (celite) and the ethanol was carefully evaporated on the rotary evaporator (some product is lost in this process). The residue was distilled to give 39 g (77 percent) of the desired aniline as a nearly colorless liquid which quickly turns yellow on standing. The product had a b.p. of 41° C. at ~1 mm. The NMR (CDCl₃) spectra was consistent with the assigned structure.

Step C

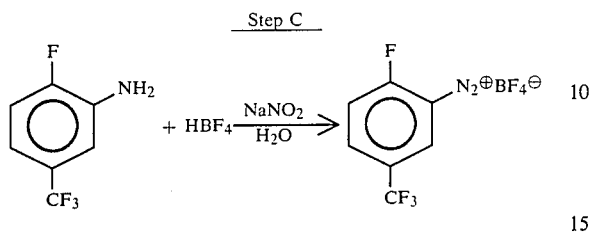

A mechanically stirred solution of 3-amino-4-fluorobenzotrifluoride (17.9 g, 0.1 mole) in 48 percent fluoboric acid (72 g ~0.4 mole of HBF₄) and water (100 ml) was cooled to ≦5° C. in an ice-salt bath. To this solution was slowly dropped a solution of sodium nitrite (7.25 g, 0.105 mole) in water (10 ml). Soon after the addition began, a solid began to separate. After about one-quarter of the sodium nitrite solution had been added, the reaction mixture had become very thick. It was necessary to stir very vigorously with an efficient stirrer in order to complete the reaction. After the addition was complete, stirring at ≦5° C. was continued for an hour, then the solid diazonium salt collected by filtration (medium porosity funnel). The salt was washed with cold 5 percent HBF₄ solution (75 ml), then with several portions of cold ether. This material was then dried overnight in a vacuum oven over P₂O₅ at 60° C. to give 22 g (79 percent) of the diazonium tetrafluoroborate (shown above) as an off-white solid. The NMR (d6-acetone) spectra was consistent with the assigned structure.

Step D

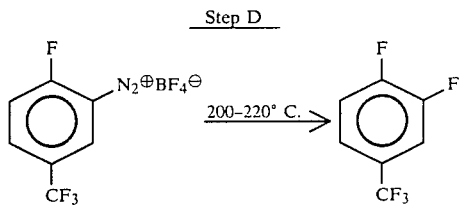

The diazonium salt (22 g) from Step E, which is shown above, was placed in a round-bottom flask (250 ml) equipped with a dean-stark trap and a condenser through which ice-water was circulated. The top of the condenser was connected to a trap containing 10 percent NaOH solution. The flask was immersed in an oil bath heated to 200°-220° C. The salt melted, turned dark and decomposed slowly, at first, then decomposed much more vigorously. The decomposition was accompanied by large amounts of gas and smoke. The desired 3,4-difluoro-benzotrifluoride which distilled was collected in the dean-stark trap as a dark red liquid (6 g). This was taken up in pentane (20 ml) which was then stirred with MgSO₄ and Na₂CO₃, filtered and distilled to give pure 3,4-difluorobenzotrifluoride (3.25 g, 22.5 percent) as a colorless liquid having a b.p. of 104° C.

Step E

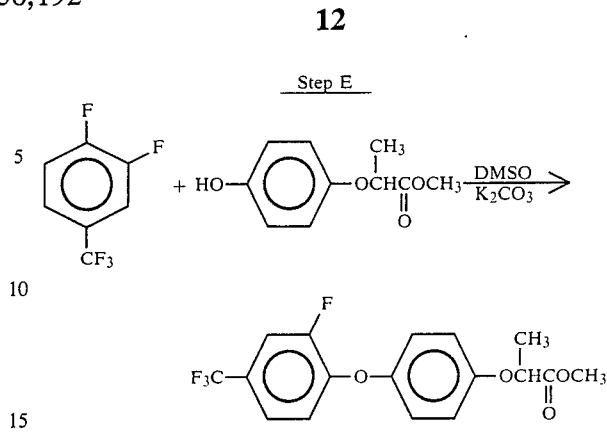

A stirred mixture of 3,4-difluorobenzotrifluoride (1.82 g, 0.01 mole), methyl 2-(4-hydroxyphenoxy)propionate (2.72 g, 0.01 mole) and potassium carbonate (1.5 g) in DMSO (20 ml) was heated at 100°-110° C. for 90 minutes. After cooling, the mixture was poured into water (200 ml), then extracted with ether (2×100 ml). Pentane (50 ml) was added to the ether extracts, and this was washed with water (200 ml). After drying (MgSO₄) the solvent was evaporated to give the desired phenoxyphenoxypropionate (2.0 g, 55.9 percent) shown above as a pale yellow oil with a refractive index (R.I.) of 1.4998 at 25° C. The NMR (CDCl₃) spectra for ¹H and ¹⁹F were consistent with the assigned structure.

EXAMPLE 2

Preparation of α[4-(4'-chloro-2'-fluorophenoxy)phenoxy]propionic acid methyl ester

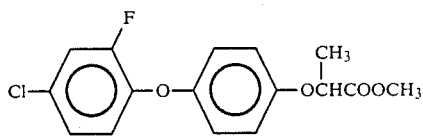

Step 2A

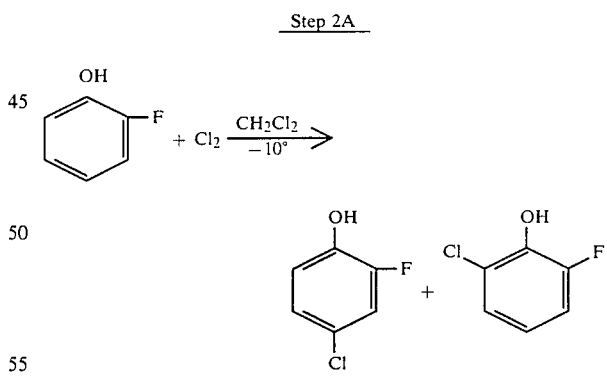

A stirred solution of 2-fluorophenol (20 g; 0.178 mole) in methylene chloride (200 ml) was cooled to ≦−10° C. in an ice-salt bath. Precondensed chlorine (12.62 g; 0.178 mole) was then slowly bubbled into the solution at such a rate that the temperature did not rise above −10° C. After all of the chlorine had been added, and the green color dissipated, the reaction was checked by gas chromatography (g.c.). Even though no chlorine remained, g.c. showed that besides the two chlorinated products, a fair amount (~25%) of the starting phenol remained. At this point there was little or no dichlorinated material present. Additional chlorine was bubbled into the reaction mixture until g.c. showed that all of the starting material had been consumed. At this point, the reaction mixture contained 3% of a dichlorinated material as well as an 8:2 mixture of monochlorinated products. The mixture was poured into water (300 ml) containing excess sodium bisulfite. The organic layer was separated, dried (MgSO₄) and the solvent evaporated to give 25.5 g of a light yellow liquid. Fluorine NMR (CDCl₃) showed that an 8:2 mixture of monochlorinated products to be present. It was presumed that the major isomer was the desired 4-chloro-2-fluorophenol and that this would react faster in nucleophillic substitution reactions than the more sterically hindered 2-chloro-6-fluorophenol. This mixture was used directly in the next reaction (Step 2B).

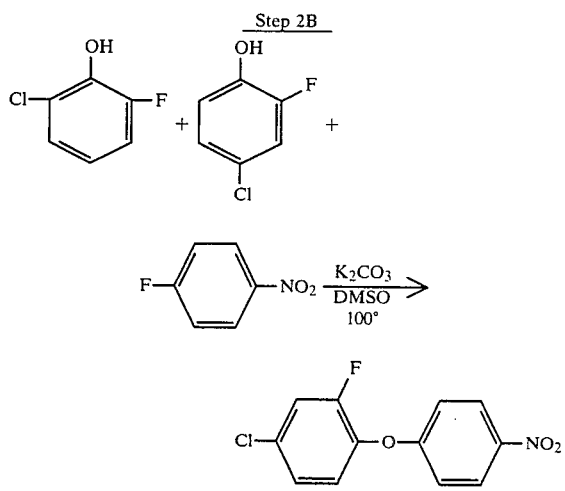

To a stirred mixture of potassium carbonate (25.04 g; 0.18 mole) in DMSO (200 ml) under an argon atmosphere was added an 8:2 mixture (25 g; 0.171 mole) (from Step 2A) of 4-chloro-2-fluorophenol (~20 g; 0.136 mole) and 2-chloro-6-fluorophenol (~5 g; 0.034 mole). To this mixture was added 4-fluoronitrobenzene (18.05 g; 0.128 mole) and the resulting mixture stirred at 100° C. for 30 minutes. At the end of this time, g.c. showed that the mixture contained (peak areas) ~10% of 2-chloro-6-fluorophenol, ~3% of a dichlorofluorophenol, a trace of 4-chloro-2-fluorophenol, and a single product peak. This mixture was poured into aqueous base (~1% NaOH) and the resulting mixture extracted with ether (2×300 ml). The ether extracts were combined, washed with water (an emulsion formed which required a little saturated aqueous NaCl to break), dried (MgSO₄) and the solvent removed to give an orange-red oil (34 g). ¹⁹F NMR (CDCl₃) showed that essentially a single isomer to be present. The material was subjected to Kugelrohr distillation (oven temp.=135°-145°) to give the desired product as a light yellow oil (32 g): RI=1.6038 ≃ 25° C. Recrystallization from hexane (freezer) gave the product as a white solid: m.p.=55°-57° C.

The carbon, hydrogen and nitrogen content was:

|  | Carbon | Hydrogen | Nitrogen |
| --- | --- | --- | --- |
| Calculated: | 53.85 | 2.64 | 5.23 |
| Found: | 53.70 | 2.54 | 5.16 |

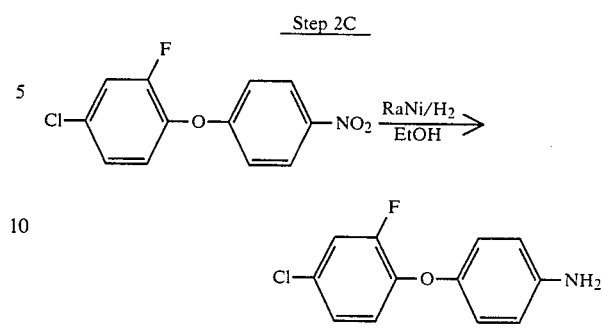

Raney Nickel, i.e., RaNi (3 scoopulas) was washed with water (2×300 ml) and then ethanol (2×300 ml). To this was added a solution of the phenoxynitrobenzene (29 g; 0.108 g) in ethanol (250 ml). The resulting mixture was hydrogenated in a Paar apparatus (initial H₂ pressure=50 psi) until the theoretical amount of hydrogen had been taken up (3–4 hours). The mixture was filtered and the solvent evaporated from the filtrate to give 25 g of a light yellow oil which solidified upon standing. An analytical sample was prepared by recrystallization from hexane: m.p.=85.5°-87° C.

The carbon, hydrogen and nitrogen content was:

|  | Carbon | Hydrogen | Nitrogen |
| --- | --- | --- | --- |
| Calculated: | 60.64 | 3.82 | 5.89 |
| Found: | 60.49 | 3.77 | 5.85 |

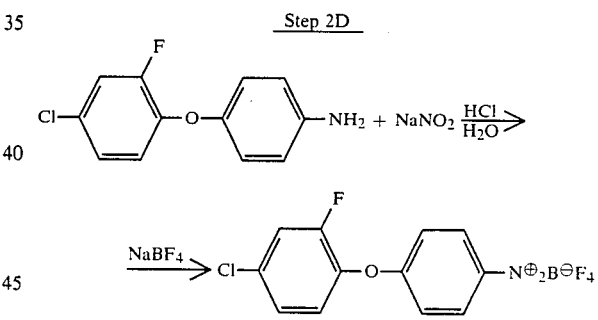

Concentrated hydrochloric acid (35 ml) was added all at once to a mechanically stirred suspension of the aniline (16.64 g; 0.07 mole) in water (70 ml) and the resulting mixture cooled to ≦5° C. in an ice bath. To this stirred mixture was slowly added (dropwise) a solution of sodium nitrite (5.0 g; 0.072 mole) in water (10 ml). The temperature was maintained at ≦8° C. during the addition. By the time the addition was complete, the mixture was essentially homogeneous. After stirring at ≦5° C. for an additional 30 minutes, the solution was treated with charcoal, then filtered through celite. The filtrate was again stirred mechanically at ≦5° C. (ice bath) and a solution of sodium fluoroborate (10.98 g; 0.1 mole) in water (35 ml) was added rapidly. A solid separated immediately. After stirring for an additional 15 minutes, the solid was filtered, washed with a small amount of ice water, then with cold ether (3×150 ml). The solid was air dried for an hour, then completely dried in a vacuum oven over P₂O₅ at 80° C. for 3 hours. There was thus obtained the desired diazonium tetrafluoroborate (19 g; 84.7%) as an off-white solid. The NMR (d6 acetone or CF₃CO₂H) of this material was consistent with the assigned structure and showed a low field, two-proton doublet for the protons ortho to the diazonium salt. This material was used directly in subsequent reactions. (Step 2E of Example 2 and Example 3).

Step 2E

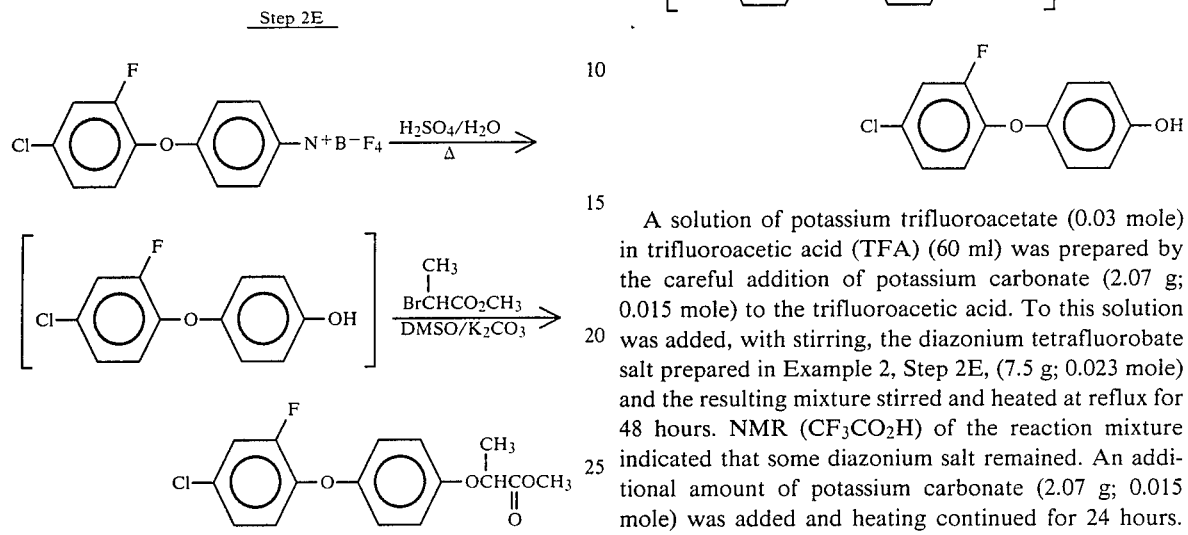

To a stirred solution of concentrated sulfuric acid (8 ml) in water (32 ml) which was heated to a gentle boil, was slowly added the above tetrafluoroborate diazonium salt (from Step 2D) (4 g; 0.0125 mole). After the addition was complete, stirring and heating was contained for 45 minutes, then the reaction poured into ice-water (~300 ml). The mixture was then extracted with ether (3×100 ml), the combined extracts dried (MgSO₄) and the solvent evaporated to give 1.2 g of a red oil. Thin layer chromatography (TLC) (silica gel, 7:3 hexane-ethyl acetate) and g.c. showed that this was one main product (phenol) contaminated by a minor product. This red oil was dissolved in DMSO (10 ml), and then methyl 2-bromopropionate (0.9 g, 0.0054 mole) and potassium carbonate (0.84 g; 0.006 mole) was added and the resulting mixture stirred under an inert atmosphere overnight. After the addition of water (200 ml), the mixture was extracted with ether (2×75 ml). The combined ether extracts were washed with water (75 ml), dried (MgSO₄) and the solvent removed to give 1.3 g of a red oil. NMR (CDCl₃) of this material was consistent with the desired α-[4-(4'-chloro-2'-fluorophenoxy)phenoxy]propionic acid methyl ester. The oil was chromatographed (130 g silica gel, 7:3 hexane-acetone), but this failed to remove the color. The material was taken up in methanol, treated with charcoal, filtered and evaporated to give a yellow oil: R.I.=1.5509.

EXAMPLE 3

Preparation of 4-(4'-chloro-2'-fluorophenoxy)phenol

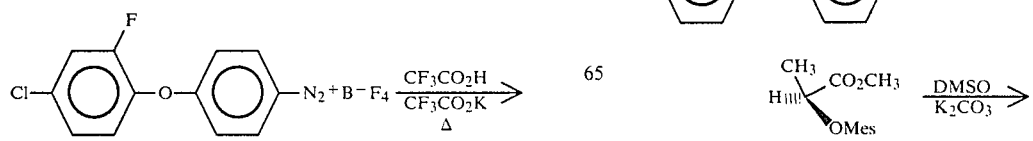

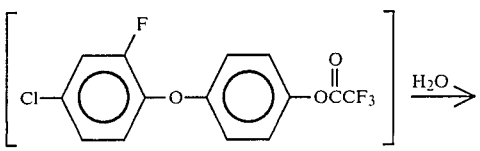

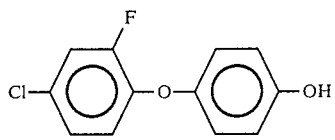

A solution of potassium trifluoroacetate (0.03 mole) in trifluoroacetic acid (TFA) (60 ml) was prepared by the careful addition of potassium carbonate (2.07 g; 0.015 mole) to the trifluoroacetic acid. To this solution was added, with stirring, the diazonium tetrafluorobate salt prepared in Example 2, Step 2E, (7.5 g; 0.023 mole) and the resulting mixture stirred and heated at reflux for 48 hours. NMR (CF₃CO₂H) of the reaction mixture indicated that some diazonium salt remained. An additional amount of potassium carbonate (2.07 g; 0.015 mole) was added and heating continued for 24 hours. Again, NMR indicated that a small amount of starting material remained. Additional K₂CO₃ (2.07 g) was added and heating continued for 24 hours. NMR now showed that the mixture was essentially devoid of starting material. About 30 ml of TFA was removed by distillation and the resulting mixture poured into water (200 ml). This aqueous mixture was stirred at 40°-45° C. for 3 hours to hydrolyze the trifluoroacetate. After cooling, the mixture was extracted with ether (3×100 ml), and the ether extracts were treated with charcoal and then filtered through a short pad of silica gel. The filtrate was evaporated to give a dark viscous residue. This was purified via HPLC (8:2 hexane-ethyl acetate) the second peak being collected. Removal of the solvent gave a viscous red oil which was homogeneous by TLC and g.c. NMR (CDCl₃) was consistent with the assigned structure. This material solidified upon standing for several days. The methodology employed in this example is analogous to the methods described in D. E. Horning et al., *Can. J. Chem.*, 51, 2347 (1973) which is incorporated herein by reference.

EXAMPLE 4

Preparation of the R enantiomer of α-[4-(4'-chloro-2'-fluorophenoxy)-phenoxy]propionic acid methyl ester

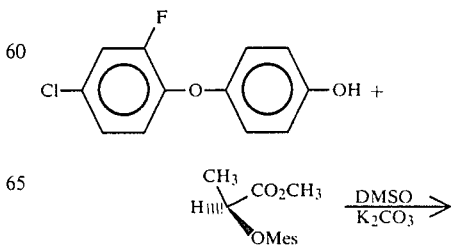

-continued

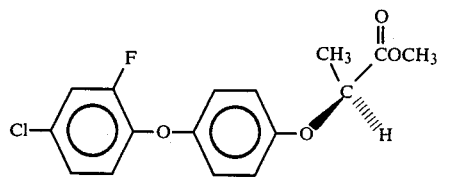

A mixture of 4-(4'-chloro-2'-fluorophenoxy)-phenol (2.23 g; 0.01 mole), the methanesulfonate of S-methyl lactate (18.22 g; 0.1 mole, minimum of 90% optical purity), and potassium carbonate (1.4 g; 0.01 mole) in DMSO (75 ml) was stirred at room temperature for 18 hours. After this period, the mixture was poured into water (500 ml) then extracted into ether (3×100 ml). The ether extracts were dried (MgSO$_4$), and the solvent evaporated. The residue was purified by preparative HPLC using 8:2 hexane-ethylacetate as the eluent. The first peak to elute (after the solvent front) was collected and the solvent evaporated. This gave 2.3 g (71%) of a light yellow oil whose $^1$H and $^{19}$F NMR (CDCl$_3$) were consistent with the assigned structure. This material possessed an optical rotation of +24.68° as measured at 25° C. The refractive index was 1.5466. Attempts to measure the optical purity using the optically active NMR shift reagent tris-[3-(trifluoromethylhydroxymethylene)-d-camphorateo]europium (III) were not successful. Based upon the optical purity of the starting lactate the optical purity is estimated to be between 75 and 95%.

EXAMPLE 5

Preparation of α[4(4'-bromo-2'-fluorophenoxy)phenoxy]propionic acid methyl ester Step I

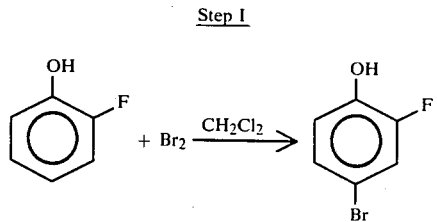

To a stirred solution of 2-fluorophenol (22.4 g, 0.2 mole) in methylene chloride (250 ml) which was cooled to ~3° C. in an ice bath, was added, all at once, bromine (31.97 g, 0.2 mole). The resulting solution was stirred at ice bath temperature for two hours and then at room temperature for 1 hour. The mixture was poured into water (600 ml) containing excess sodium bisulfite. The organic phase was separated and the aqueous phase was washed with additional methylene chloride (200 ml). The combined organic extracts were washed with saturated sodium bicarbonate, dried (MgSO$_4$) and the solvent evaporated to give the desired 2-fluoro-4-bromophenol as a colorless oil (34.5 g, 90%). The NMR (CDCl$_3$) was consistent with the assigned structure. The gc of this material showed that it contained only a trace of the 2,6-isomer. This material was used directly in the following step without additional purification.

Step II

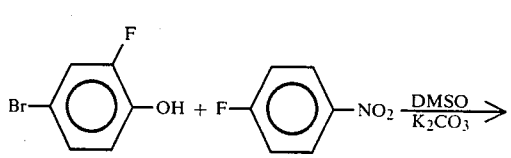

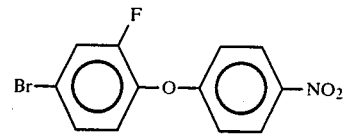

To a stirred mixture of 2-fluoro-4-bromophenol (34.0 g, 0.178 mole), and 4-fluoronitrobenzene (25.12 g, 0.178 mole) in DMSO (250 ml) was added powdered potassium carbonate (27.8 g, 0.2 mole). The resulting mixture was maintained under an atmosphere of argon and warmed to 100° C. (oil bath temp) for one hour. After cooling, the mixture was poured into an ice-cold, 1N NaOH solution (1000 ml) and extracted with ether (3×250 ml). The ether extracts were combined, washed with water (300 ml), dried (MgSO$_4$) and the solvent evaporated to give a yellow oil. This material was crystallized from hexane-ether to yield 44.5 g (80%) of the desired product as a light yellow-crystalline solid: m.p.=62°-64° C.; NMR (CDCl$_3$) was consistent with the assigned structure. The carbon, hydrogen and nitrogen content was as follows:

|  | Carbon | Hydrogen | Nitrogen |
| --- | --- | --- | --- |
| Calculated: | 46.18 | 2.26 | 4.49 |
| Found: | 46.11 | 2.22 | 4.50 |

Step III

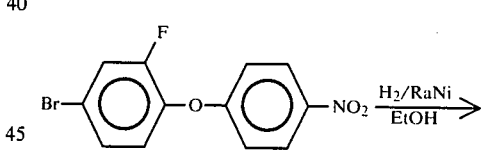

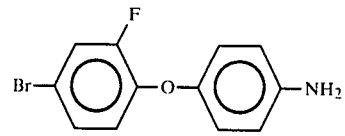

Raney nickel (3 spoonulas) was washed with water (3×250 ml) and then ethanol (3×200 ml). To the catalyst covered with a small amount of ethanol, was added a solution of the 4-(4'-bromo-2'-fluorophenoxy)nitro benzene from Step III (9.36 g, 0.03 mole) dissolved in warm ethanol (75 ml). The solution was degassed with argon, then hydrogenated on a Parr apparatus with an initial hydrogen pressure of 50 psi. When the theoretical volume of hydrogen had been consumed (~90 minutes), the mixture was degassed, and the catalyst removed via filtration (celite). The solvent was evaporated to give a white solid. Upon recrystallization of this material from methylcyclohexane, it took on an orange coloration and the recrystallized product was tinted orange. A small amount which was recrystallized from hexane did not undergo this apparent slight decomposition. Regardless of the color, the NMR (CDCl₃) was consistent with the desired product: m.p.=98°–99.5° C.; Yield=7.7 g (91%). The carbon, hydrogen and nitrogen content was as follows:

|  | Carbon | Hydrogen | Nitrogen |
|---|---|---|---|
| Calculated: | 51.08 | 3.22 | 4.97 |
| Found: | 51.10 | 3.09 | 4.80 |

This material was used in the next reaction step.

STEP IV

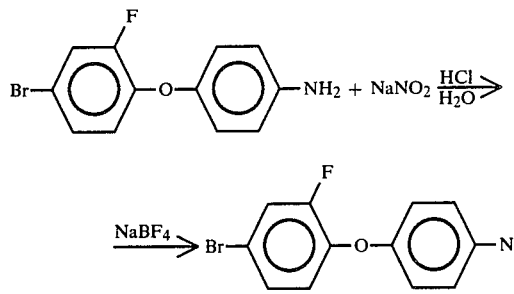

Concentrated hydrochloric acid (50 ml), (was added all at once to a stirred suspension of 4-(4-bromo-2'-fluorophenoxy)aniline (30 g, 0.106 mole) in water (110 ml). The resulting mixture was cooled to ~3° C. in an ice bath and then a solution of sodium nitrite (8.07 g, 0.117 mole) in water (15 ml) was slowly added. During the addition, the temperature was maintained at ≦8° C. When all of the sodium nitrite had been added, the mixture had become a homogeneous solution. After the addition was complete, the mixture was stirred at 3° C. for 20 minutes, treated with charcoal, and filtered through celite. The cold filtrate was poured into a 1-liter erlynmeyer flask (wide-mouth), equipped with a mechanical stirrer, and cooled in an ice bath. To this solution, vigorously stirred, was added a solution of sodium fluoroborate (17.6 g, 0.16 mole) in water (50 ml). A white precipitate separated immediately and the mixture was almost too thick to stir. Stirring was continued for 15 minutes, then the product filtered (medium porosity funnel), washed with several portions of ice water and then with cold ether (3×100 ml). After air drying for 30 minutes, the product was dried in a vacuum oven over P₂O₅ at 80° C. for 3 hours. There was thus obtained 37.5 g (84%) of the desired diazonium salt, i.e., 4-(4'-bromo-2'-fluorophenoxy)phenyl diazonium tetrafluoroborate as a white solid. The NMR (CF₃CO₂H) was consistent with the assigned structure. This material was used directly in the next reaction step.

STEP V

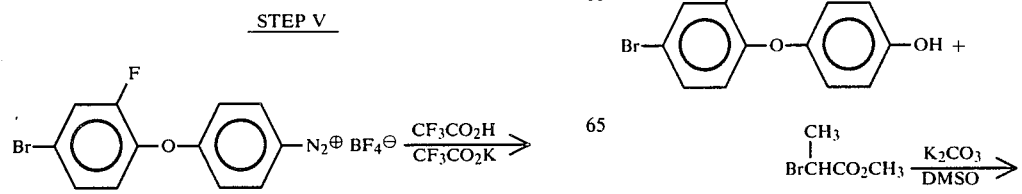

STEP V

-continued

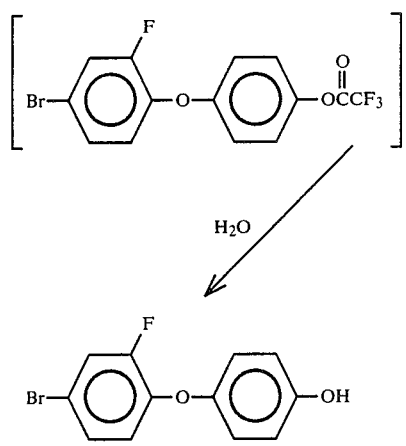

Potassium carbonate (34.78 g, 0.25 mole) was carefully and slowly added to trifluoroacetic acid (200 ml). After the reaction had ceased, the diazonium salt (37 g, 0.097 mole) from Step IV was added, and the stirred solution heated at reflux for 18 hours. At the end of this period, the NMR of the reaction mixture showed the absence of any starting diazonium salt. About half of the trifluoroacetic acid was distilled, then the residue poured into water (600 ml). This mixture was stirred at 50°–60° C. for 1 hour, cooled, and extracted with ether (3×200 ml). The ether extracts were combined, washed with water, and then with saturated sodium bicarbonate (3×300 ml). The sodium bicarbonate wash was conducted carefully because of the generation of foam. The ether phase was then treated with charcoal and filtered through a short pad of silica gel. The ether was removed to give a yellow-orange oil. The pure phenol was obtained by prep HPLC (7:3 hexane-ethylacetate) with the second peak being collected (1-recycle). Removal of the solvent gave the desired product as an orange oil (19 g, 69%) whose NMR was consistent with the assigned structure. RI=1.6056 @ 25° C. The carbon and hydrogen content was as follows:

|  | Carbon | Hydrogen |
|---|---|---|
| Calculated: | 50.91 | 2.85 |
| Found: | 51.20 | 2.89 |

STEP VI

-continued
STEP VI

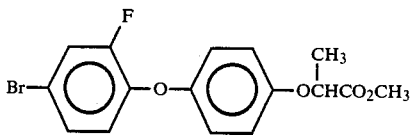

A mixture of the 4-(4'-bromo-2'-fluorophenoxy)-phenol (5.66 g, 0.02 mole) from Step V, methyl 2-bromoproprionate (3.34 g, 0.02 mole) and potassium carbonate (3.06 g, 0.22 mole) in DMSO (30 ml) was stirred, under an atmosphere of nitrogen, at room temperature for 18 hours. The mixture was poured into water (300 ml), and the resulting mixture extracted with ether (2×100 ml). The ether extracts were combined, washed with water (100 ml), dried (MgSO$_4$), and the solvent evaporated to give the desired α[4-(4'-bromo-2'-fluorophenoxy)phenoxy]propionic acid methyl ester as a yellow oil (6.0 g, 81%); R.I.=1.5628; NMR (CDCl$_3$) was consistent with the assigned structure. The carbon and hydrogen content was as follows:

|             | Carbon | Hydrogen |
|-------------|--------|----------|
| Calculated: | 52.05  | 3.82     |
| Found:      | 52.12  | 3.64     |

EXAMPLE 6

Preparation of the R enantiomer of α[4-(4'-bromo-2'-fluorophenoxy)phenoxy]propionic acid methyl ester

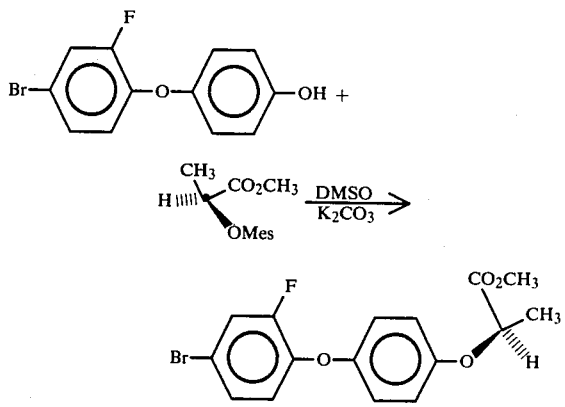

A mixture of the 4(4'-bromo-2'-fluorophenoxy)-phenol (2.83 g, 0.01 mole), the methanesulfonate of S methyl lactate (18.2 g, 0.01 mole), and potassium carbonate (1.67 g, 0.012 mole) in DMSO (70 ml) was stirred at room temperature for 40 hours, then poured into water (700 ml). The mixture was extracted with ether (2×200 ml). Pentane (100 ml) was added to the combined ether extracts and the resulting solution washed with water (300 ml). The organic phase was dried (MgSO$_4$) and the solvent evaporated to give a light yellow oil (~7 g). This oil was purified via prep HPLC (8:2 hexane-acetone) with the first peak being collected. Removal of the solvent gave the desired product enriched in the "R" enantiomer; Optical rotation=+20.34° @ 25° C. R.I.=1.5614 @ 25° C.; NMR (CDCl$_3$) was identical with that obtained in Example 4.

No attempt was made to determine the optical purity of this material.

The compounds of the present invention, i.e., active ingredients, have been found to be suitable for use in methods for the preemergent and postemergent control of grasses, such as, barnyard grass, crabgrass, yellow foxtail and johnson grass, in the presence of broadleaf crops, such as, cotton, soybeans and sugar beets. Further, it has been surprisingly found that the compounds of Formula (I) above where X is —Cl or —Br are selective, i.e., exhibit little or no phytotoxic effects, to small grains, such as, wheat and barley.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic 61 (molecular weight about 1000), polyethylene glycol ester of tall oil acids, sodium octophenoxyethoxyethyl sulfate, tris(polyoxyethylene)-sorbitan monostearate (Tween 60), and sodium dihexyl-sulfosuccinate.

The concentration of the active ingredients in solid or liquid compositions generally is from about 0.003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power dusters, boom and hand sprayers, spray dusters, by addition to irrigation water, and by other conventional means. The compositions can also be applied from airplanes as a dust or spray since the active ingredients are effective at very low application rates.

The active ingredients of the present invention have been found to possess desirable herbicidal activity in general against grassy weeds such as foxtail, blackgrass, wild oats, barnyard grass and crabgrass in preemergent operations and also against the same grasses in postemergent operations. The active ingredients possess desirable herbicidal activity against the grassy weeds, described above, while at the same time are tolerant or selective to broadleaf crops, such as, cotton, soybeans and sugar beets. The compounds of Formula (I) where X is —Cl or —Br are surprisingly tolerant or selective to small grain crops, such as, wheat and barley.

The exact rate to be applied is dependent not only on a specific active ingredient being applied, but also on a particular action desired (e.g., general or selective control), the plant species to be modified, and the stage of growth thereof as well as the part of the plant to be contacted with the toxic active ingredient. Thus, it is to be understood that all of the active ingredients of the present invention and compositions containing the same may not be equally effective at similar concentrations or against the same plant species. In non-selective pre-emergence and foliar treatments, the active ingredients of the invention are usually applied at an approximate rate of from about 0.1 to about 5 pounds/acre, but higher rates may be appropriate in some cases such as 20 pounds/acre or more. In preemergent operations for selective uses a dosage of about 0.01 to about 10 pounds/acre or more is generally applicable, a rate of 0.05 to 4 pounds/acre being preferred and about 0.1 to about 2 pounds/acre being most preferred. For controlling an infestation of annuals, a dosage of about 0.1 to 0.5 pound/acre is generally utilized. When the infestation consists largely of perennials, a dosage of from 0.1 to 4, preferably 0.5 to 2.0 pounds/acre should be employed.

In postemergent operations a dosage of about 0.01 to about 20 pounds/acre or more is generally applicable, although not all compounds are equally effective and some weeds are more difficult to control. A dosage rate in the range of about 0.05 to about 0.75 pounds/acre is preferred in selective postemergent control of annual grassy weeds, while about 0.25 to about 5 pounds/acre is preferred and more preferably about 0.25 to about 2 pounds/acre for the selective postemergent control of perennial grassy weeds.

EXAMPLE A

Postemergent Activity

Representative compositions of the present invention were evaluated for the postemergence control of species of plants listed in Table A. In these evaluations, plots of the plant species listed in Table A, grown to a height of about 4 inches, were used. Aqueous spray compositions, containing various amounts of α[4-(2'-fluoro-4'-trifluoromethylphenoxy)phenoxy]propionic acid methyl ester, i.e., 125 ppm, 62.5 ppm, 31.25 ppm, 15.6 ppm, 7.8 ppm and 3.9 ppm, respectively, were applied to separate plots. The spray compositions were made by mixing the active ingredient in acetone to ½ the final volume, i.e., twice the final concentration. An equal amount of water was added to the active ingredient/acetone mixture wherein the water contained 0.1 percent by weight of TWEEN ® 20 surfactant. The application to the plants was made to the point of run-off (125 ppm provides approximately 0.3125 lb active ingredient per acre) and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated on a scale of 0 to 100 where 0 represents no effect and 100 represents complete kill. The results of the examination of the treated plots are set forth below in Table A.

TABLE A

Percent Kill and Control of Plants at Various Concentrations (ppm) of α[4-(2'-fluoro-4'-trifluoromethylphenoxy)phenoxy]propionic Acid Methyl Ester

| Plant | Control | Concentration (ppm) | | | | | |
| --- | --- | --- | --- | --- | --- | --- | --- |
| | | 125 | 62.5 | 31.25 | 15.6 | 7.8 | 3.9 |
| Corn | 0 | 100 | 100 | 100 | 100 | 30 | 20 |
| Rice | 0 | 100 | 100 | 100 | 85 | 30 | 0 |
| Sorghum | 0 | 100 | 100 | 100 | 100 | 100 | 70 |

TABLE A-continued

Percent Kill and Control of Plants at Various Concentrations (ppm) of α[4-(2'-fluoro-4'-trifluoromethylphenoxy)phenoxy]propionic Acid Methyl Ester

| Plant | Control | Concentration (ppm) | | | | | |
|---|---|---|---|---|---|---|---|
| | | 125 | 62.5 | 31.25 | 15.6 | 7.8 | 3.9 |
| Wheat | 0 | 100 | 100 | 100 | 90 | 60 | 0 |
| Barnyard Grass | 0 | 100 | 100 | 100 | 100 | 100 | 50 |
| Crabgrass | 0 | 100 | 100 | 100 | 100 | 100 | 90 |
| Yellow Foxtail | 0 | 100 | 100 | 100 | 100 | 100 | 35 |
| Johnson Grass | 0 | 100 | 100 | 100 | 100 | 100 | 60 |
| Wild Oats | 0 | 100 | 100 | 100 | 60 | 0 | 0 |

At 125 ppm α[4-(2'-fluoro-4'-trifluoromethylphenoxy)phenoxy]propionic acid methyl ester was inactive, i.e., no phytotoxic effect, against cotton, rape, soybeans, sugar beets, jimson weed, morning glory, pigweed, velvet leaf and cocklebur.

EXAMPLE B

Postemergent Activity

Substantially the same procedures as those described in Example A were repeated except that the active ingredient was α[4-(4'-chloro-2'-fluorophenoxy)phenoxy]propionic acid methyl ester. The results are listed below in Table B.

TABLE B

Percent Kill and Control of Plants at Various Concentrations (ppm) of α[4-(4'-chloro-2'-fluorophenoxy)phenoxy]propionic Acid Methyl Ester

| Plant | Control | Concentration (ppm) | | | | | |
|---|---|---|---|---|---|---|---|
| | | 250 | 125 | 62.5 | 31.25 | 15.6 | 7.8 |
| Corn | 0 | 100 | 100 | 30 | 0 | 0 | 0 |
| Rice | 0 | 75 | 20 | 0 | 0 | 0 | 0 |
| Sorghum | 0 | 98 | 20 | 5 | 0 | 0 | 0 |
| Wheat | 0 | 0 | 0 | 0 | 0 | 0 | 0 |
| Barnyard Grass | 0 | 100 | 100 | 100 | 100 | 100 | 90 |
| Crabgrass | 0 | 95 | 30 | 60 | 20 | 5 | 0 |
| Yellow Foxtail | 0 | 80 | 95 | 70 | 45 | 0 | 0 |
| Johnson Grass | 0 | 75 | 15 | 0 | 0 | 0 | 0 |
| Wild Oats | 0 | 40 | 40 | 0 | 0 | 0 | 0 |

At 125 ppm α[4-(4'-chloro-2'-fluorophenoxy)phenoxy]propionic acid methyl ester was inactive against cotton, rape, soybeans, sugar beets, jimson weed, morning glory, pigweed, velvet leaf and cocklebur.

EXAMPLE C

Postemergent Activity

Substantially the same procedures as those described in Example A were repeated except that the active ingredient was the R enantiomer of α[4-(4'-chloro-2'-fluorophenoxy)phenoxy]propionic acid methyl ester. The results are listed below in Table C.

TABLE C

Percent Kill and Control of Plants at Various Concentrations (ppm) of the R enantiomer of α[4-(4'-chloro-2'-fluorophenoxy)phenoxy]propionic Acid Methyl Ester

| Plant | Control | Concentration (ppm) | | | | | |
|---|---|---|---|---|---|---|---|
| | | 250 | 125 | 62.5 | 31.25 | 15.6 | 7.8 |
| Corn | 0 | 100 | 100 | 100 | 60 | 15 | 0 |
| Rice | 0 | 60 | 15 | 0 | 0 | 0 | 0 |
| Sorghum | 0 | 100 | 90 | 60 | 40 | 0 | 0 |
| Wheat | 0 | 0 | 0 | 0 | 0 | 0 | 0 |
| Barnyard Grass | 0 | 100 | 100 | 100 | 100 | 100 | 75 |
| Crabgrass | 0 | 100 | 100 | 98 | 100 | 95 | 20 |
| Yellow Foxtail | 0 | 100 | 100 | 95 | 95 | 50 | 0 |
| Johnson Grass | 0 | 75 | 75 | 30 | 10 | 0 | 0 |
| Wild Oats | 0 | 60 | 35 | 20 | 0 | 0 | 0 |

At 250 ppm no phytotoxicity was exhibited by α[4-(4'-chloro-2'-fluorophenoxy)phenoxy]propionic acid methyl ester against cotton, rape, soybeans, sugar beets, jimson weed, morning glory, pigweed, velvet leaf and cocklebur.

EXAMPLE D

Preemergent Activity

In a representative operation, α[4-(2'-fluoro-4'-trifluoromethylphenoxy)phenoxy]propionic acid methyl ester, to be utilized in a series of tests, is dissolved in acetone to one half of the final volume (twice the final concentration) to be used and the acetone solution in each case is admixed with an equal volume of water containing 0.1 percent by weight of Tween-20 surface active material (Tween-20 is a trademark of Atlas Chemical Company). The composition, generally in the nature of an emulsion, was employed to treat separate respective seed beds of sandy loam soil of good nutrient content wherein each seed bed contained separate groups of good viable seeds, each group being of one of a known plant species. The various beds were positioned side by side and exposed to substantially identical conditions of temperature and light. Each bed was maintained so as to prevent any interaction with the test compound in different seed beds. Each seed bed was treated with the composition as a spray employing conventional spraying equipment to deposit a predetermined amount of the compound uniformly throughout the surface of the bed. Another seed bed was treated only with the acetone-Tween-20 water mixture with no chemical added to serve as a control. After treatment, the seed beds were maintained for two weeks under greenhouse conditions conducive for good plant growth and watered as necessary. The specific plant species, dosage and the percent preemergent control obtained are set forth in Table D below. Control refers to the reduction in growth of the test species in the presence of the test chemical relative to the observed growth of the same species in the absence of the test chemical.

TABLE D

Premergence Control of Plant Species (%) Exhibited by α[4-(2'-fluoro-4'-trifluoromethyl-phenoxy)-phenoxy]propionic Acid Methyl Ester

| Dosage in Lbs. Per Acre | Corn | Rice | Sorghum | Wheat | Barnyard Grass | Crab Grass | Johnson Grass | Wild Oats | Yellow Foxtail |
|---|---|---|---|---|---|---|---|---|---|
| 0.25 | 100 | 100 | 100 | 100 | 100 | 100 | 100 | 100 | 100 |
| 0.125 | 100 | 100 | 100 | 100 | 100 | 100 | 100 | 100 | 100 |
| 0.062 | 90 | 90 | 100 | 90 | 80 | 100 | 90 | 90 | 100 |
| 0.031 | 50 | 30 | 30 | 20 | 70 | 100 | 60 | 20 | 70 |
| 0.016 | 20 | 0 | 10 | 0 | 20 | 40 | 20 | 0 | 20 |

At 0.25 lbs/acre the compound listed in Table D above was inactive, i.e., no phytotoxic effect, against the seeds of velvet leaf, rape, cotton, soybean, pigweed, jimson weed, sugarbeets and yellow nutsedge.

EXAMPLE E

Preemergent Activity of Racemic (R,S) α[4-(4'-chloro-2'-fluorophenoxy)phenoxy]propionic Acid Methyl Ester and its R enantiomer Substantially the same procedures described in Example D were repeated using as the active ingredients
(1) racemic (R,S) α[4-(4'-chloro-2'-fluorophenoxy)phenoxy]propionic acid methyl ester and
(2) (R) α[4-(4'-chloro-2'-fluorophenoxy)phenoxy]propionic acid methyl ester.
The results of the preemergence tests are listed in Table E below.

TABLE E

Preemergence Control of Plant Species (%) Exhibited by Racemic (R,S) α[4-(4'-Chloro-2'-fluorophenoxy)phenoxy]propionic Acid Methyl Ester and its R enantiomer

| Dosage in Lbs. Per Acre | Corn R,S | Corn R | Rice R,S | Rice R | Sorghum R,S | Sorghum R | Wheat R,S | Wheat R | Barnyard Grass R,S | Barnyard Grass R | Crabgrass R,S | Crabgrass R | Johnson Grass R,S | Johnson Grass R | Wild Oats R,S | Wild Oats R | Yellow Foxtail R,S | Yellow Foxtail R |
|---|---|---|---|---|---|---|---|---|---|---|---|---|---|---|---|---|---|---|
| 1 | 95 | 95 | 100 | 100 | 50 | 98 | 0 | 20 | 100 | 100 | 100 | 100 | 80 | 98 | 70 | 80 | 95 | 98 |
| 0.5 | 95 | 95 | 100 | 100 | 70 | 80 | 0 | 10 | 100 | 100 | 100 | 100 | 60 | 95 | 50 | 60 | 95 | 95 |
| 0.25 | 90 | 90 | 95 | 100 | 10 | 10 | 0 | 0 | 98 | 98 | 100 | 100 | 0 | 80 | 20 | 0 | 90 | 30 |
| 0.125 | 70 | 0 | 95 | 98 | 0 | 0 | 0 | 0 | 98 | 10 | 100 | 98 | 0 | 0 | 0 | 0 | 10 | 0 |
| 0.062 | 0 | 0 | 0 | 30 | 0 | 0 | 0 | 0 | 40 | 0 | 60 | 70 | 0 | 0 | 0 | 0 | 0 | 0 |

At 1 lb/acre the compounds listed in Table E above were inactive, i.e., no phytotoxic effect, against the seeds of velvet leaf, rape, cotton, soybean, pigweed, jimson weed, sugarbeets and yellow nutsedge.

EXAMPLE F

Postemergent Activity

Substantially the same procedures as those described in Example A were repeated except that the active ingredient was α[4-(4'-bromo-2'-fluorophenoxy)phenoxy]propionic acid methyl ester. The results are listed below in Table F.

TABLE F

Percent Kill and Control of Plants at Various Concentrations (ppm) of α[4-(4'-bromo-2'-fluorophenoxy)-phenoxy]propionic Acid Methyl Ester

| Plant | Control | 500 | 250 | 125 | 62.5 | 31.25 | 15.6 |
|---|---|---|---|---|---|---|---|
| Corn | 0 | 100 | 100 | 100 | 70 | 10 | 0 |
| Rice | 0 | 99 | 95 | 99 | 90 | 65 | 35 |
| Sorghum | 0 | 100 | 100 | 45 | 35 | 0 | 0 |
| Wheat | 0 | 0 | 0 | 0 | 0 | 0 | 0 |
| Barnyard Grass | 0 | 100 | 100 | 100 | 100 | 100 | 100 |
| Crabgrass | 0 | 90 | 40 | 20 | 0 | 0 | 0 |
| Yellow Foxtail | 0 | 95 | 80 | 15 | 0 | 0 | 0 |
| Johnson Grass | 0 | 40 | 25 | 15 | 0 | 0 | 0 |
| Wild Oats | 0 | 80 | 75 | 10 | 0 | 0 | 0 |

At 125 ppm α[4-(4'-bromo-2'-fluorophenoxy)phenoxy]propionic acid methyl ester was inactive against cotton, rape, soybeans, sugar beets, jimson weed, morning glory, pigweed, velvet leaf and cocklebur.

The compounds of the present invention contain an optically active center as shown in Formula (I) (2 position of the propanoic acid) and can exist in optically active steroisomeric forms such as the dextrorotatory and levorotatory forms of each of the above configurations. The various mixtures and racemates, i.e., enantiomers, isomers are within the scope of the present invention.

In further embodiments, the compounds of the present invention or compositions containing the same, can be advantageously employed in combination with one or more additional pesticidal compounds. Such additional pesticidal compounds may be insecticides, nematocides, anthropodicides, herbicides, fungicides or bactercides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

What is claimed is:

1. A compound of the formula

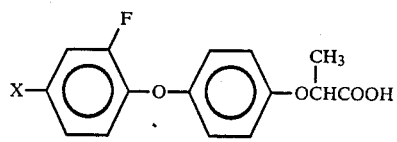

wherein
X represents —Cl, —CF$_3$, —I, —Br, —OCF$_3$, —CF$_2$Cl, —CF$_2$H or —CF$_2$CCl$_2$H, and agriculturally acceptable salts, amides, and esters thereof.

2. The compound of claim 1 which is the R enantiomer.

3. The compound of claim 1 wherein X is —Cl, —Br or —CF$_3$.

4. The compound of claim 3 wherein X is —CF$_3$.

5. The compound of claim 4 which is α[4-(2'-fluoro-4'-trifluoromethylphenoxy)phenoxy]propionic acid or an agriculturally acceptable salt or ester thereof.

6. The compound of claim 5 which is the R enantiomer.

7. The compound of claim 5 which is the methyl, ethyl, n-propyl or butyl ester.

8. The compound of claim 7 which is α[4-(2'-fluoro-4'-trifluoromethylphenoxy)phenoxy]propionic acid methyl ester.

9. The compound of claim 8 which is the R enantiomer.

10. The compound of claim 2 wherein X is —Cl.

11. The compound of claim 10 which is α[4-(4'-chloro-2'-fluorophenoxy)phenoxy]propionic acid or an agriculturally acceptable salt or ester thereof.

12. The compound of claim 11 which is the R enantiomer.

13. The compound of claim 11 which is the methyl, ethyl, n-propyl or butyl ester.

14. The compound of claim 13 which is α[4-(4'-chloro-2'-fluorophenoxy)phenoxy]propionic acid methyl ester.

15. The compound of claim 14 which is the R enantiomer.

16. The compound of claim 3 wherein X is —Br.

17. The compound of claim 16 which is α[4-(4'-bromo-2'-fluorophenoxy)phenoxy]propionic acid or an agriculturally acceptable salt or ester thereof.

18. The compound of claim 17 which is the R enantiomer.

19. The compound of claim 17 which is the methyl, ethyl, n-propyl or butyl ester.

20. The compound of claim 19 which is α[4-(4'-bromo-2'-fluorophenoxy)phenoxy]propionic acid methyl ester.

21. The compound of claim 20 which is the R enantiomer.

22. A method of controlling weeds which comprises applying to the weeds a herbicidally effective amount of one or more compounds described in claim 1 or claim 8.

23. The method of claim 22 wherein the active compound is α[4-(2'-fluoro-4'-trifluoromethylphenoxy)phenoxy]propionic acid or an agriculturally acceptable salt, amide or ester thereof or mixtures thereof.

24. The method of claim 23 wherein the active compound is the R enantiomer.

25. The method of claim 23 wherein the active compound is α[4-(2'-fluoro-4'-trifluoromethylphenoxy)phenoxy]propionic acid methyl ester.

26. The method of claim 25 wherein the active compound is the R enantiomer.

27. The method of claim 22 wherein the active compound is α[4-(4'-chloro-2'-fluorophenoxy)phenoxy]propionic acid or an agriculturally acceptable salt, amide or ester thereof or mixtures thereof.

28. The method of claim 27 wherein the active compound is the R enantiomer.

29. The method of claim 27 wherein the active compound is α[4-(4'-chloro-2'-fluorophenoxy)phenoxy]propionic acid methyl ester.

30. The method of claim 29 wherein the active compound is the R enantiomer.

31. The method of claim 29 carried out in the presence of a small grain crop.

32. The method of claim 31 wherein the small grain crop is wheat or barley.

33. The method of claim 22 wherein the active compound is α[4-(4'-bromo-2'-fluorophenoxy)phenoxy]propionic acid or an agriculturally acceptable salt, amide or ester thereof or mixtures thereof.

34. The method of claim 33 wherein the active compound is the R enantiomer.

35. The method of claim 33 wherein the active compound is α[4-(4'-bromo-2'-fluorophenoxy)phenoxy]propionic acid methyl ester.

36. The method of claim 35 wherein the active compound is the R enantiomer.

37. The method of claim 33 carried out in the presence of a small grain crop.

38. The method of claim 37 wherein the small grain crop is wheat or barley.

39. A herbicidal composition which comprises
(a) a herbicdally effective amount of one or more compounds described in claim 1 or claim 8 and
(b) an agriculturally acceptable adjuvant.

40. The composition of claim 39 wherein the active compound is α[4-(2'-fluoro-4'-trifluoromethylphenoxy)phenoxy]propionic acid or an agriculturally acceptable salt, amide or ester thereof or mixtures thereof.

41. The composition of claim 40 wherein the active compound is the R enantiomer.

42. The composition of claim 40 wherein the active compound is α[4-(2'-fluoro-4'-trifluoromethylphenoxy)phenoxy]propionic acid methyl ester.

43. The composition of claim 50 wherein the active compound is the R enantiomer.

44. The composition of claim 47 wherein the active compound is α[4-(4'-chloro-2'-fluorophenoxy)phenoxy]propionic acid or an agriculturally acceptable salt, amide or ester thereof or mixtures thereof.

45. The composition of claim 52 wherein the active compound is the R enantiomer.

46. The composition of claim 53 wherein the active compound is α[4-(4'-chloro-2'-fluorophenoxy)phenoxy]propionic acid methyl ester.

47. The composition of claim 54 wherein the active compound is the R enantiomer.

48. The composition of claim 52 which is to be applied to weeds present in a small grain crop.

49. The composition of claim 56 wherein the small grain crop is wheat or barley.

50. The composition of claim 47 wherein the active compound is α[4-(4'-bromo-2'-fluorophenoxy]propionic acid or an agriculturally acceptable salt, amide or ester thereof or mixtures thereof.

51. The composition of claim 58 wherein the active compound is the R enantiomer.

52. The composition of claim 58 wherein the active compound is α[4-(4'-bromo-2'-fluorophenoxy)phenoxy]propionic acid methyl ester.

53. The composition of claim 60 wherein the active compound is the R enantiomer.

54. The composition of claim 58 which is to be applied to weeds present in a small grain crop.

55. The composition of claim 62 wherein the small grain crop is wheat or barley.

* * * * *

UNITED STATES PATENT AND TRADEMARK OFFICE
CERTIFICATE OF CORRECTION

PATENT NO. : 4,550,192  
DATED : October 29, 1985  
INVENTOR(S) : Richard B. Rogers; B. Clifford Gerwick, III Page 1 of 2

It is certified that error appears in the above-identified patent and that said Letters Patent is hereby corrected as shown below: PAGE ONE OF TWO Column 4, line 1, insert in right side of column --(13)--.
Column 6, line 41, "z" should read "Z".
Column 7, line 18, "-CL" should read -- -Cl --.
Column 13, line 59, "≃" should read --@--.
Column 16, line 20, "tetrafluorobate" should read --tetrafluoroborate--.
Column 18, line 28, "yellow-crystalline" should read --yellow crystalline--.
Column 19, line 29, "4-(4-bromo-2'-" should read -- 4-(4'-bromo-2'- --.
Column 22, line 62, "bentonite" should read --bentonite,--.
Column 27, line 2, "Premergence" should read --Preemergence--.
Column 28, line 58, "anthropodicides," should read --arthropodicides,--; line 59, "tercides" should read --tericides--.
Column 30, line 37, "herbicdally" should read --herbicidally--; line 49, "claim 50" should read --claim 42--; line 51, "claim 47" should read --claim 39--; line 55, "claim 52" should read --claim 44--; line 57, "claim 53" should read --claim 45--; line 60, "claim 54" should read --claim 46--; line 62, "claim 52" should read --claim 44--; line 64, "claim 56" should read --claim 48--; line 66, "claim 47" should read --claim 39--.

UNITED STATES PATENT AND TRADEMARK OFFICE
CERTIFICATE OF CORRECTION

PATENT NO. : 4,550,192

DATED : October 29, 1985

INVENTOR(S) : Richard B. Rogers; B. Clifford Gerwick, III

It is certified that error appears in the above-identified patent and that said Letters Patent is hereby corrected as shown below: PAGE TWO OF TWO

```
Column 31, line 3, "claim 58" should read --claim 50--;
line 5, "claim 58" should read --claim 50--.
Column 32, line 1, "claim 60" should read --claim 52--;
line 3, "claim 58" should read --claim 50--; line 5,
"claim 62" should read --claim 54--.
```

Signed and Sealed this

Twenty-sixth Day of August 1986

[SEAL]

Attest:

DONALD J. QUIGG

Attesting Officer

Commissioner of Patents and Trademarks